(12) United States Patent
Hagiwara (10) Patent No.: US 7,359,476 B2
(45) Date of Patent: Apr. 15, 2008

(54) RADIATION TOMOGRAPHIC IMAGING APPARATUS AND RADIATION TOMOGRAPHIC IMAGING METHOD, AND IMAGE PRODUCING APPARATUS

(75) Inventor: Akira Hagiwara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 382 days.

(21) Appl. No.: 10/924,291

(22) Filed: Aug. 23, 2004

(65) Prior Publication Data

US 2005/0053187 A1    Mar. 10, 2005

(30) Foreign Application Priority Data

Sep. 9, 2003  (JP)  ............ 2003-317086

(51) Int. Cl.
*A61B 6/03*  (2006.01)
(52) U.S. Cl. ............ 378/4; 378/901; 382/131
(58) Field of Classification Search ............ 378/4, 378/15, 901; 382/131
See application file for complete search history.

(56) References Cited

U.S. PATENT DOCUMENTS

| | | | |
|---|---|---|---|
| 4,868,843 A | | 9/1989 | Nunan |
| 5,319,551 A | * | 6/1994 | Sekiguchi et al. ......... 382/131 |
| 5,663,995 A | * | 9/1997 | Hu ............ 378/15 |
| 5,933,540 A | * | 8/1999 | Lakshminarayanan et al. ............ 382/260 |
| 6,178,223 B1 | | 1/2001 | Solomon et al. |
| 6,205,350 B1 | | 3/2001 | Lorenz et al. |
| 6,459,754 B1 | | 10/2002 | Besson et al. |
| 6,480,565 B1 | | 11/2002 | Ning |
| 6,542,572 B2 | | 4/2003 | Danielsson et al. |
| 7,068,837 B2 | | 6/2006 | Befu et al. |
| 2006/0064396 A1 | * | 3/2006 | Wei et al. ............ 707/1 |

FOREIGN PATENT DOCUMENTS

| | | |
|---|---|---|
| EP | 0424912 A2 | 5/1991 |
| JP | 08-055210 | 2/1996 |
| JP | 11-167622 | 6/1999 |
| JP | 2002-153454 | 5/2002 |

OTHER PUBLICATIONS

European Patent Office Search Report; 154282/10222; 04255380.0-1526-; GE Medical Systems Global Technology Company LLC; 3 pgs.
Ralph Muller; "Computer in Medicine: Materials and Methods"; 7-18, Mar. 2005; Institute for Biomedical Engineering, Mar. 2005; 6 pgs.
Abstract and English Translation of JP08-055210 (13 pgs.).
Abstract and English Translation of JP11-167622 (10 pgs.).

\* cited by examiner

*Primary Examiner*—Edward J. Glick
*Assistant Examiner*—John M Corbett
(74) *Attorney, Agent, or Firm*—Armstrong Teasdale LLP

(57) ABSTRACT

A method and apparatus for reducing image noise, increasing image resolution, and facilitating reduced exposure to a subject to be imaged or improved apparatus life. A radiation tomographic imaging apparatus comprises, as image producing means, inter-imaging-plane filtering processing means for acquiring image data for a plurality of planes generated corresponding to imaging planes that are a plurality of cross-sectional planes of a subject to be imaged, and conducting filtering processing on the image data across the plurality of imaging planes. The filtering processing across the imaging planes that are a plurality of cross-sectional planes facilitates discrimination between a specific shape present in the cross-sectional plane and noise.

19 Claims, 9 Drawing Sheets

RADIATION TOMOGRAPHIC IMAGING APPARATUS AND RADIATION TOMOGRAPHIC IMAGING METHOD, AND IMAGE PRODUCING APPARATUS

CROSS REFERENCE TO RELATED APPLICATIONS

This application claims the benefit of Japanese Application No. 2003-317086 filed Sep. 9, 2003.

BACKGROUND OF THE INVENTION

The present invention relates to a radiation tomographic imaging apparatus and radiation tomographic imaging method, and an image producing apparatus and image producing method.

Known radiation tomographic imaging apparatuses include an X-ray CT (computed tomography) apparatus that employs X-ray radiation to produce an image representing a cross-sectional plane of a subject to be imaged. The X-ray CT apparatus is used in a wide variety of applications including medical and industrial applications with a human body or an inanimate object as a subject to be imaged.

The X-ray CT apparatus scans a subject to be imaged around the body axis direction of the subject to be imaged, and emits X-rays from a predetermined position around the subject to be imaged toward an imaging region in the subject to be imaged along an imaging plane that is a cross-sectional plane. Radiation passing through the subject to be imaged is detected at a predetermined position around the subject to be imaged to acquire detected data, and image data for the cross-sectional plane is generated based on the detected data.

The regions in the subject to be imaged and the purpose of imaging with the X-ray CT apparatus are becoming increasingly diverse, and, accordingly, the X-ray CT apparatus is required to have improved image quality including resolution and increased imaging speed. To respond to such requirements, an X-ray CT apparatus comprising a multi-row detector has been developed, in which the multi-row detector has a plurality of rows of detector elements for detecting X-rays arranged in the body axis direction of the subject to be imaged. The X-ray CT apparatus comprising the multi-row detector is sometimes referred to in the art as an MDCT (Multi-row Detector CT) apparatus.

The MDCT apparatus has several advantages: for example, since it has the multi-row detector having a plurality of rows of detector elements arranged in the body axis direction that corresponds to the slice thickness direction, thus offering a wide coverage per unit time, images representing a plurality of cross-sectional planes can be simultaneously acquired; and since the slice thickness of a cross-sectional plane can be arbitrarily selected, a high-definition image representing a cross-sectional plane of fine slice thickness can be produced.

As opposed to these advantages, the amount of emitted X-rays for one imaging plane corresponding to a cross-sectional plane is decreased to reduce exposure of the subject to be imaged in the MDCT apparatus, and the produced image therefore tends to contain noise.

Figure 9A:
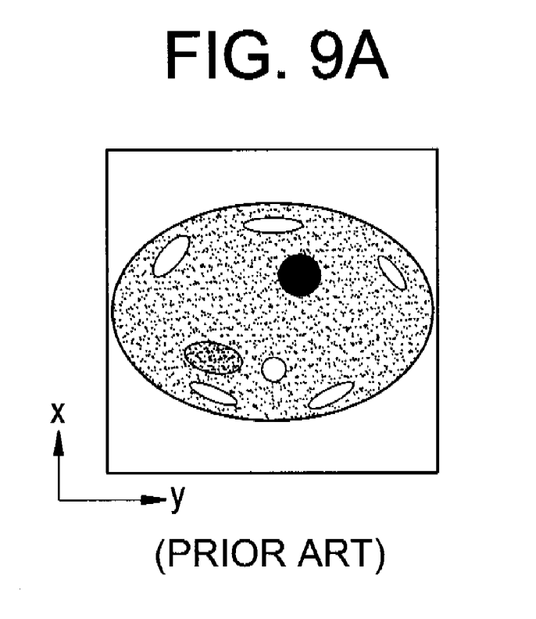
FIG. 9 is a diagram showing a conventional method for conducting filtering processing on image data.
Figure 9B:
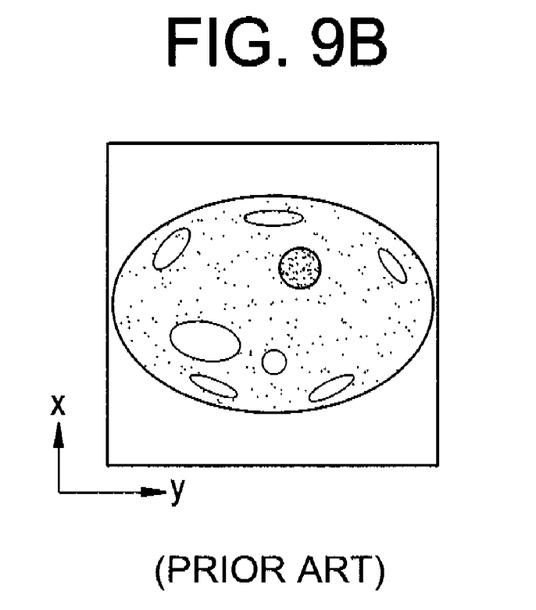

To reduce noise in the produced image, a variety of methods have been proposed (see Patent Document 1, for example). FIG. 9 is a diagram showing a conventional method of conducting filtering processing on image data. In the drawing, FIG. 9(a) shows an image before filtering processing, and FIG. 9(b) shows the image after filtering processing. As shown in FIG. 9, the conventional filtering processing is conducted in an X-Y plane that corresponds to the same imaging plane for the subject to be imaged. For the filtering processing, smoothing processing is conducted, for example.

[Patent Document 1] Japanese Patent Application Laid Open No. 2002-153454.

The smoothing processing involves calculating an average value between a prespecified pixel in an imaging plane and another pixel proximate to the prespecified pixel, and using the average value as image data for the prespecified pixel. Since the amount of information on one pixel can be increased by using image data of a proximate pixel, the technique can reduce noise in the imaging plane.

Filtering processing, such as smoothing processing, on the image of FIG. 9(a) can provide an image with reduced noise as shown in FIG. 9(b). As opposed to the reduction of noise, the image often has a reduced resolution and is blurred because the filtering processing is conducted in an X-Y plane that corresponds to the same imaging plane for the subject to be imaged.

Another method that may be contemplated to reduce noise in a produced image is to increase the X-ray exposure dose to the subject to be imaged to enhance contrast and improve sensitivity. However, this method leads to other problems, for example, the increase of radiation exposure to the subject to be imaged, and adverse effect on the X-ray tube life due to an increase in the amount of heat in the X-ray tube for generating X-rays.

As described above, since the conventional techniques conduct filtering processing in an X-Y plane that corresponds to the same imaging plane for the subject to be imaged, it is difficult to achieve a combination of reduced image noise and improved resolution, reduced exposure to a subject to be imaged, or improved apparatus life.

SUMMARY OF THE INVENTION

It is therefore an object of the present invention to provide a radiation tomographic imaging apparatus and radiation tomographic imaging method, and an image producing apparatus and image producing method that can easily achieve a combination of reduced image noise and improved resolution, reduced exposure to a subject to be imaged, or improved apparatus life.

To attain the aforementioned object, a radiation tomographic imaging apparatus of the present invention comprises: radiation emitting means for scanning a subject to be imaged around a body axis direction of said subject to be imaged and emitting radiation to an imaging region in said subject to be imaged; radiation detecting means for detecting said radiation passing through said subject to be imaged; and image producing means for generating image data representing said imaging region based on said detected radiation, wherein said image producing means comprises inter-imaging-plane filtering processing means for acquiring said image data for a plurality of planes generated corresponding to imaging planes that are a plurality of cross-sectional planes of said imaging region, and conducting filtering processing on said image data across said plurality of imaging planes.

As described above, the radiation tomographic imaging apparatus of the present invention acquires image data for a plurality of planes generated corresponding to imaging planes that are a plurality of cross-sectional planes of a subject to be imaged, and conducts filtering processing on the image data across the plurality of imaging planes.

To attain the aforementioned object, a radiation tomographic imaging method of the present invention employs a radiation tomographic imaging apparatus comprising radiation emitting means for scanning a subject to be imaged around a body axis direction of said subject to be imaged and emitting radiation to an imaging region in said subject to be imaged, and radiation detecting means for detecting said radiation passing through said subject to be imaged, and the radiation tomographic imaging method comprises an image producing step of generating image data representing said imaging region based on radiation detected by said radiation detecting means, wherein said image producing step comprises an inter-imaging-plane filtering processing step of acquiring said image data for a plurality of planes generated corresponding to imaging planes that are a plurality of cross-sectional planes of said subject to be imaged, and conducting filtering processing on said image data across said plurality of imaging planes.

As described above, the radiation tomographic imaging method of the present invention acquires image data for a plurality of planes generated corresponding to imaging planes that are a plurality of cross-sectional planes of a subject to be imaged, and conducts filtering processing on the image data across the plurality of imaging planes.

To attain the aforementioned object, an image producing apparatus of the present invention generates image data representing an imaging region in a subject to be imaged, and comprises inter-imaging-plane filtering processing means for acquiring said image data for a plurality of planes generated corresponding to a plurality of imaging planes of said imaging region, and conducting filtering processing on said image data across said plurality of imaging planes.

As described above, the image producing apparatus of the present invention acquires image data for a plurality of planes generated corresponding to a plurality of imaging planes for a subject to be imaged, and conducts filtering processing on the image data across the plurality of imaging planes.

To attain the aforementioned object, an image producing method of the present invention generates image data representing an imaging region in a subject to be imaged, and comprises an inter-imaging-plane filtering processing step of acquiring said image data for a plurality of planes generated corresponding to a plurality of imaging planes of said imaging region, and conducting filtering processing on said image data across said plurality of imaging planes.

As described above, the image producing method of the present invention acquires image data for a plurality of planes generated corresponding to a plurality of imaging planes for a subject to be imaged, and conducts filtering processing on the image data across the plurality of imaging planes.

According to the present invention, there is provided a radiation tomographic imaging apparatus and radiation tomographic imaging method, and an image producing apparatus and image producing method that can easily achieve a combination of reduced image noise and improved resolution, or reduced exposure to a subject to be imaged.

Further objects and advantages of the present invention will be apparent from the following description of the preferred embodiments of the invention as illustrated in the accompanying drawings.

DETAILED DESCRIPTION OF THE INVENTION

An exemplary embodiment of the present invention will be described below.

Figure 1:
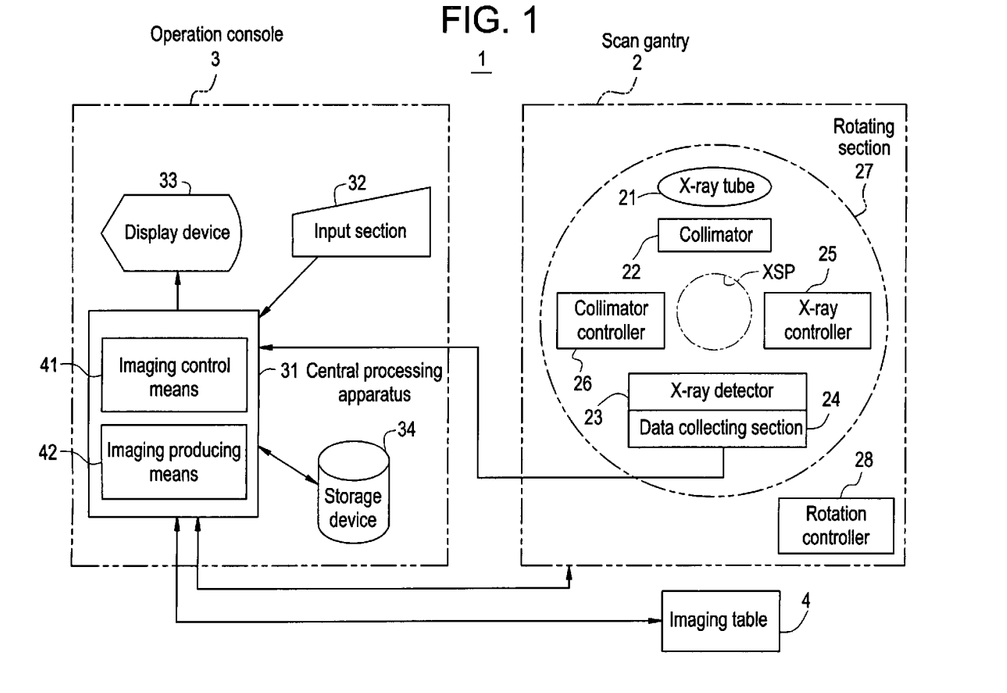
FIG. 1 is a block diagram showing the configuration of a radiation tomographic imaging apparatus in accordance with an embodiment of the present invention.

FIG. 1 is a block diagram showing the overall configuration of an X-ray CT apparatus 1 serving as a radiation tomographic imaging apparatus in accordance with an embodiment of the present invention. As shown in FIG. 1, the X-ray CT apparatus 1 of the present embodiment comprises a scan gantry 2, an operation console 3, and an imaging table 4.

The scan gantry 2 comprises an X-ray tube 21, a collimator 22, an X-ray detector 23 that is a radiation detector, a data collecting section 24, an X-ray controller 25, a collimator controller 26, a rotating section 27, and a rotation controller 28.

The X-ray tube 21 emits X-rays of predetermined intensity based on a control signal from the X-ray controller 25.

The collimator 22 forms the X-rays emitted from the X-ray tube 21 into a fan beam that has a fan-like shape having a certain width and a certain thickness, for example, based on a control signal from the collimator controller 26.

Figure 2:
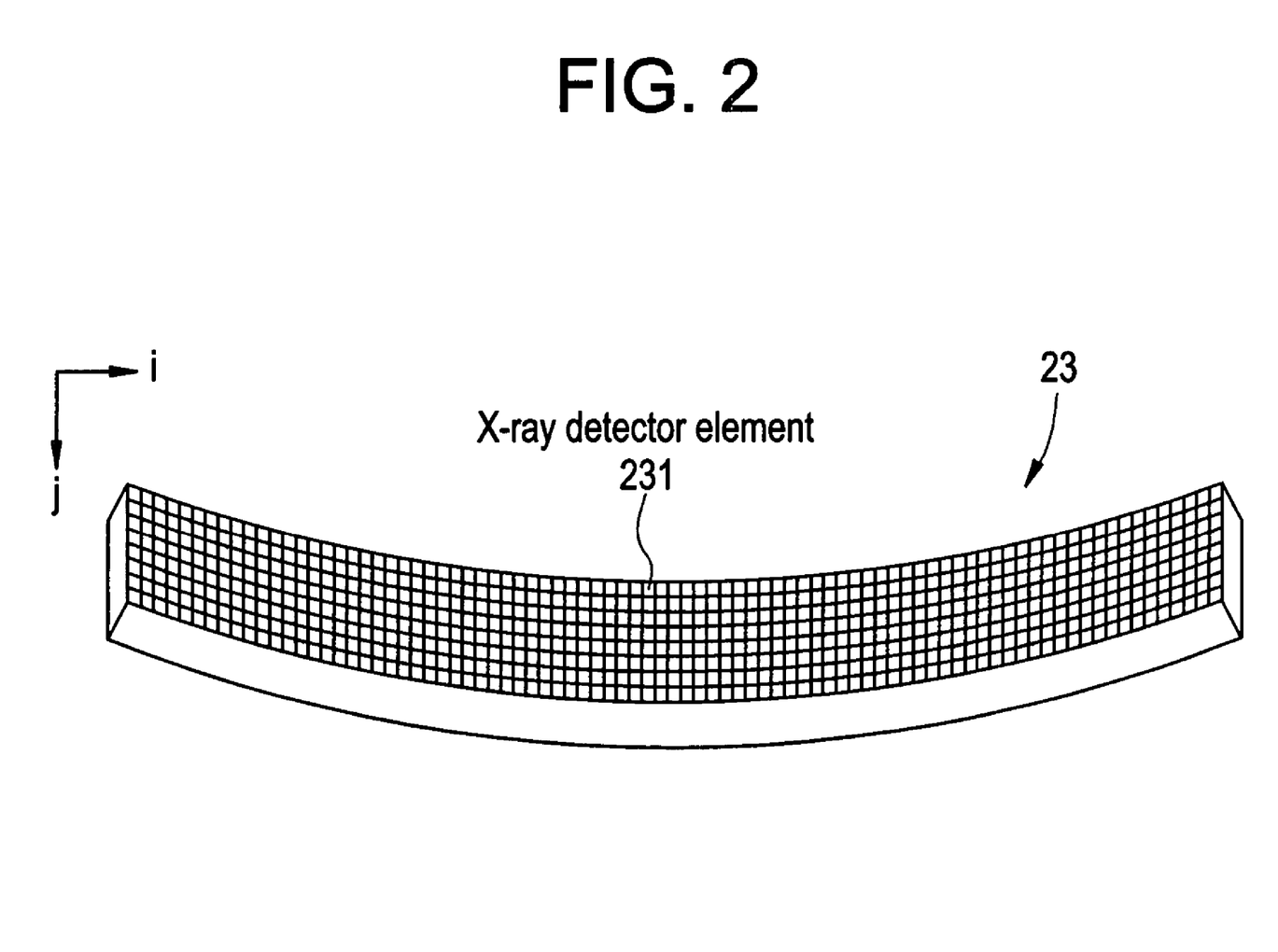
FIG. 2 is a diagram showing an exemplary configuration of an X-ray detector in accordance with the embodiment of the present invention.

FIG. 2 is a diagram showing an exemplary configuration of the X-ray detector 23 of the present embodiment. The X-ray detector 23 has a plurality of X-ray detector elements 231 arranged in a two-dimensional array in a channel direction i and a body axis direction j that corresponds to the slice thickness direction. The present embodiment thus represents an MDCT apparatus comprising a multi-row detector in which a plurality of X-ray detector elements for detecting X-rays passing through the subject to be imaged are arranged in the body axis direction of the subject to be imaged. Moreover, the X-ray detector 23 has a cylindrical concave surface formed for detecting the fan-beam X-rays.

The X-ray detector elements 231 are each made of a combination of a scintillator and a photodiode, for example. The X-ray detector elements 231 are, however, not limited to having such a configuration but may be, for example, semiconductor X-ray detector elements employing a cadmium-tellurium (CdTe) or ionization chamber X-ray detector elements employing xenon (Xe) gas.

The data collecting section 24 is connected to the X-ray detector 23, and collects detected data detected by the individual X-ray detector elements 231 in the X-ray detector 23. The data collecting section 24 converts the collected data from an analog signal to a digital signal and outputs it to a central processing apparatus 31 in the operation console 3.

The X-ray controller 25 outputs a control signal to the X-ray tube 21 in response to a control signal from the central processing apparatus 31 in the operation console 3 to control X-ray emission.

The collimator controller 26 outputs a control signal to the collimator 22 in response to a control signal from the central processing apparatus 31 in the operation console 3 to regulate the degree of opening of an aperture of the collimator 22.

The rotating section 27 supports the X-ray tube 21, collimator 22, X-ray detector 23, data collecting section 24, X-ray controller 25, and collimator controller 26. The center of the rotating section 27 forms an X-ray irradiated space XSP toward which X-rays from the X-ray tube 21 are emitted. The imaging table 4 having the subject to be imaged lying thereon is moved into the X-ray irradiated space XSP in conducting imaging. The X-ray tube 21 and X-ray detector 23 are positioned on the rotating section 27 facing each other across the X-ray irradiated space XSP. Moreover, the rotating section 27 rotates in a predetermined direction based on a control signal from the rotation controller 28.

The rotation controller 28 outputs a control signal to the rotating section 27 in response to a control signal from the central processing apparatus 31 in the operation console 3 to rotate the rotating section 27 in the predetermined direction for a desired number of rotations. In this manner, the subject to be imaged is scanned around the body axis direction of the subject to be imaged, and an imaging region in the subject to be imaged is exposed to X-rays emitted from the X-ray tube 21. X-rays passing through the subject to be imaged are then detected using the X-ray detector 23.

The operation console 3 comprises the central processing apparatus 31, an input device 32, a display device 33, and a storage device 34.

The central processing apparatus 31 is comprised of a microcomputer, for example. The central processing apparatus 31 has imaging control means 41 for coordinating operations of the scan gantry 2 and imaging table 4 to control imaging on an imaging plane, and image producing means 42 for generating image data representing the imaging plane using detected data from the X-ray detector 23 collected by the data collecting section 24.

The imaging control means 41 outputs, in response to instructions supplied from the input device 32, a control signal to the imaging table 4 having the subject to be imaged lying thereon, for carrying the imaging table 4 into and out of the X-ray irradiated space XSP in the scan gantry 2, and thus drives the imaging table 4. The imaging control means 41 also outputs a control signal to the scan gantry 2 in response to instructions supplied from the input device 32 to control the operations of the X-ray tube 21, collimator 22, X-ray detector 23, data collecting section 24, and rotating section 27. In this manner, the subject to be imaged is scanned around the body axis direction of the subject to be imaged, and radiation is emitted in a planar direction of the imaging plane that is a cross-sectional plane of the subject to be imaged. The radiation passing through the subject to be imaged is then detected. It should be noted that the imaging control means 41 can conduct control to helically scan the subject to be imaged around and along the body axis direction of the subject to be imaged.

The image producing means 42 is means for generating image data representing an imaging plane based on detected X-rays. The image producing means 42 performs image reconstruction based on detected data for a plurality of views collected by the data collecting section 24 to generate multi-slice image data for a plurality of cross-sectional planes, and displays them on the display device 33. The image data generated by the image reconstruction are stored in the storage device 34.

Figure 3:
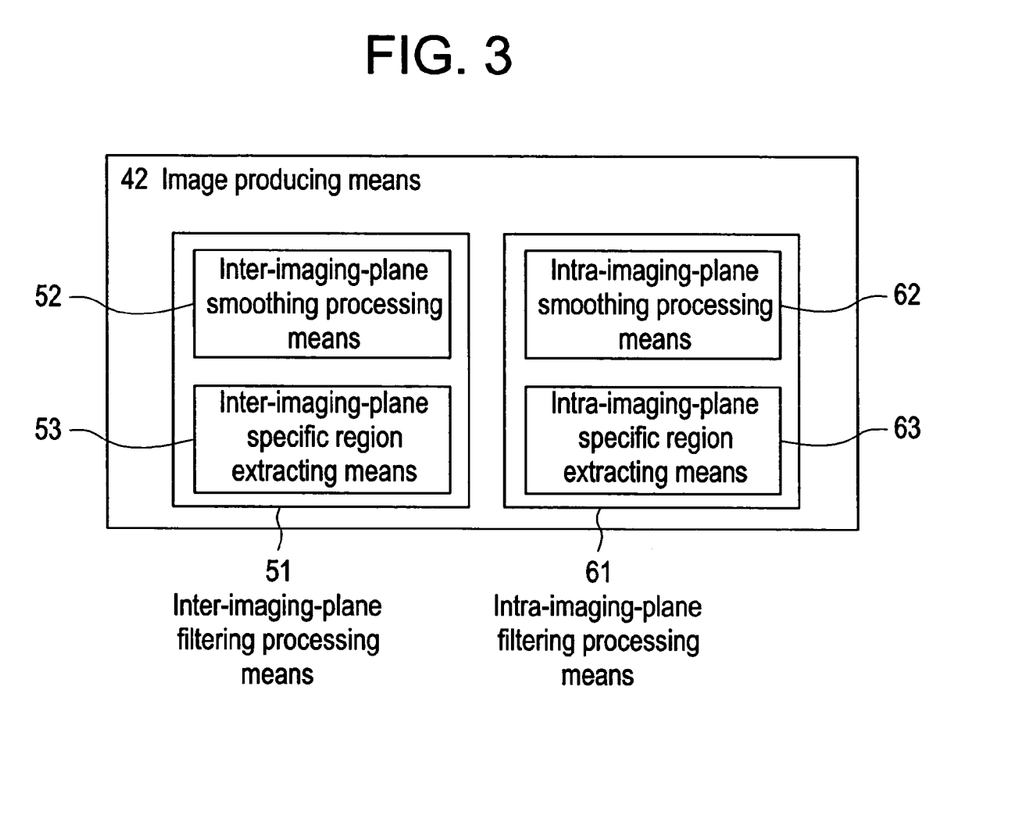
FIG. 3 is a block diagram showing image producing means 42 in accordance with the present embodiment.

FIG. 3 is a block diagram showing the image producing means 42 of the present embodiment. As shown in FIG. 3, the image producing means 42 of the present embodiment comprises inter-imaging-plane filtering processing means 51 and intra-imaging-plane filtering processing means 61.

The inter-imaging-plane filtering processing means 51 is means for acquiring image data for a plurality of planes generated corresponding to imaging planes that are a plurality of cross-sectional planes of an imaging region of the subject to be imaged, and conducting filtering processing on the image data across the plurality of imaging planes. As such inter-imaging-plane filtering processing means 51, it comprises inter-imaging-plane smoothing processing means 52 and inter-imaging-plane specific region extracting means 53.

The inter-imaging-plane smoothing processing means 52 is means for conducting smoothing processing on image data between corresponding pixel regions across the plurality of imaging planes. The inter-imaging-plane specific region extracting means 53 is means for extracting a specific pixel region in imaging planes based on the image data representing the plurality of imaging planes and a threshold defined across the plurality of imaging planes.

The inter-imaging-plane filtering processing means 61 is means for conducting filtering processing on image data in the same imaging plane for the subject to be imaged. As such intra-imaging-plane filtering processing means 61, it comprises intra-imaging-plane smoothing processing means 62 and intra-imaging-plane specific region extracting means 63.

The intra-imaging-plane filtering processing means 61 is means for conducting filtering processing on image data in the same imaging plane for the subject to be imaged. As such intra-imaging-plane filtering processing means 61, it comprises intra-imaging-plane smoothing processing means 62 and intra-imaging-plane specific region extracting means 63.

The input device 32 is provided for an operator to input desired imaging conditions to the central processing apparatus 31, and is comprised of a keyboard and mouse, for example.

The display device 33 receives image data from the central processing apparatus 31 and displays an image, and other information of several kinds.

The storage device 34 stores several kinds of data, reconstructed images and programs etc., and the stored data is accessed by the central processing apparatus 31 as required.

In the present embodiment, the X-ray tube 21 corresponds to the radiation emitting means of the present invention. The X-ray detector 23 corresponds to the radiation detecting means of the present invention, and the image producing means 42 corresponds to the image producing means and image producing apparatus of the present invention.

A radiation tomographic imaging method by the X-ray CT apparatus 1 serving as the radiation tomographic imaging apparatus of the present embodiment will now be described. The imaging method by the X-ray CT apparatus 1 of the present embodiment sequentially executes a radiation emitting/detecting step and an image producing step.

To execute these steps, the operator first inputs imaging condition data and image producing condition data using the input device 32. For the imaging condition data, the operator inputs a scan scheme, such as an axial or helical scan, scan start and end positions in the body axis direction, the number of scans, the scan speed, the amount of emitted X-rays, and the width of emitted X-rays, for example. For the image producing condition data, the operator inputs several conditions including the position in the subject to be imaged of which an image is to be produced, the slice thickness, the number of slices, and an image reconstruction algorithm. These imaging condition data and image producing condition data are output from the input device 32 to the central processing apparatus 31.

The radiation emitting/detecting step is a step of scanning the subject to be imaged around the body axis direction of the subject to be imaged, emitting radiation to an imaging region in the subject to be imaged to cause the radiation to pass through the imaging region, and detecting the radiation passing through the subject to be imaged. In this embodiment, X-rays are emitted as the radiation, and a helical scan is conducted in which the subject to be imaged is helically scanned around and along the body axis direction of the subject to be imaged. By conducting the helical scan, a range having a large slice thickness can be imaged at a high speed.

In the radiation emitting/detecting step, the imaging table 4 having the subject to be imaged lying thereon is moved into the X-ray irradiated space XSP in the scan gantry 2 based on a control signal from the central processing apparatus 31. The scan gantry 2 causes the X-ray tube 21 to emit X-rays in a plurality of view directions around subject to be imaged while rotating the rotating section 27 based on a control signal from the central processing apparatus 31.

The X-rays emitted from different directions around the subject to be imaged and passing through the subject to be imaged are detected using the X-ray detector 23 to obtain detected data. The X-ray detector 23 of the present embodiment is a multi-row detector, and can obtain detected data corresponding to a plurality of tomographic images by one rotation around the subject to be imaged and emission of X-rays from different directions around the subject to be imaged. The detected data detected by the X-ray detector 23 is collected into the data collecting section 24. The data collecting section 24 amplifies the detected data, A-D converts it, and outputs it to the central processing apparatus 31.

After the radiation emitting/detecting step, the image producing step is executed. The image producing step is a step of generating image data representing an imaging plane based on detected radiation. In the image producing step, image reconstruction is conducted using the image producing means 42 based on the detected data collected by the data collecting section 24 for the plurality of views to generate multi-slice image data representing a plurality of cross-sectional planes. The image reconstruction is carried out by applying helical weighting, and thereafter a filtered backprojection technique, for example. The image data generated by the image reconstruction is stored in the storage device 34.

In the present embodiment, the image producing step comprises an inter-imaging-plane filtering processing step and an intra-imaging-plane filtering processing step.

The inter-imaging-plane filtering processing step is a step of acquiring image data for a plurality of planes corresponding to imaging planes that are a plurality of cross-sectional planes of the subject to be imaged, and conducting filtering processing on the image data across the plurality of imaging planes. As such an inter-imaging-plane filtering processing step, an inter-imaging-plane smoothing processing step and an inter-imaging-plane specific region extracting step are executed. The inter-imaging-plane smoothing processing step is a step of conducting smoothing processing on the image data between corresponding pixel regions across the plurality of imaging planes. The inter-imaging-plane specific region extracting step is a step of extracting a specific pixel region in an imaging plane based on the image data representing the plurality of imaging planes and a threshold defined across the plurality of imaging planes.

The inter-imaging-plane filtering processing step will now be described with reference to FIGS. 4, 5 and 6.

Figure 4:
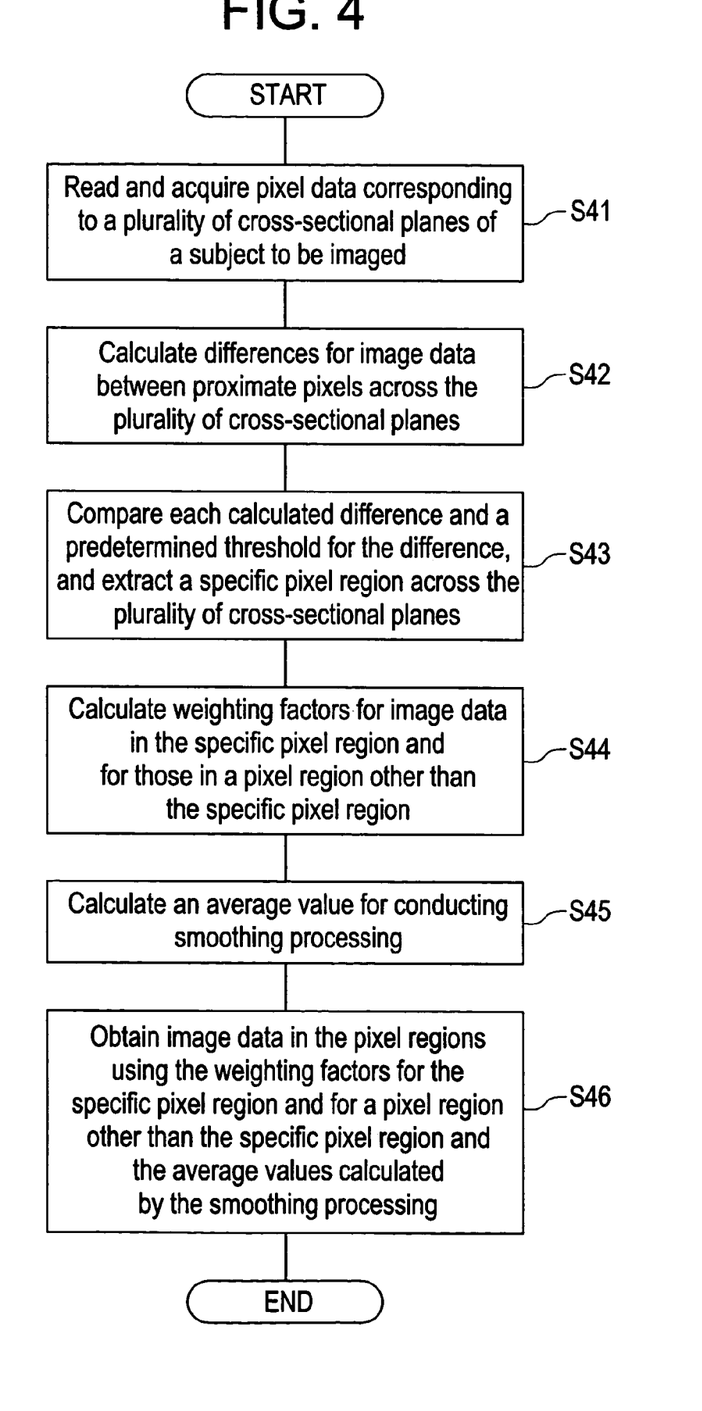
FIG. 4 is a process chart showing the procedure at an inter-imaging-plane filtering processing step.

FIG. 4 is a process chart showing the procedure at the inter-imaging-plane filtering processing step.

Figure 5A:
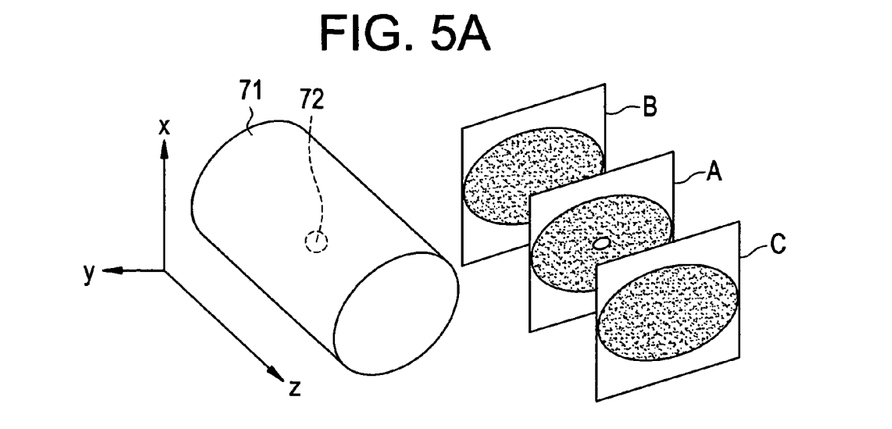
FIG. 5 is a diagram for explaining the inter-imaging-plane filtering processing step.
Figure 5B:
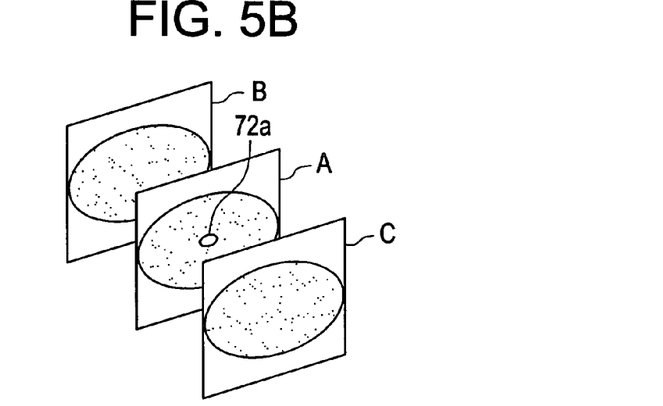
Figure 5C:
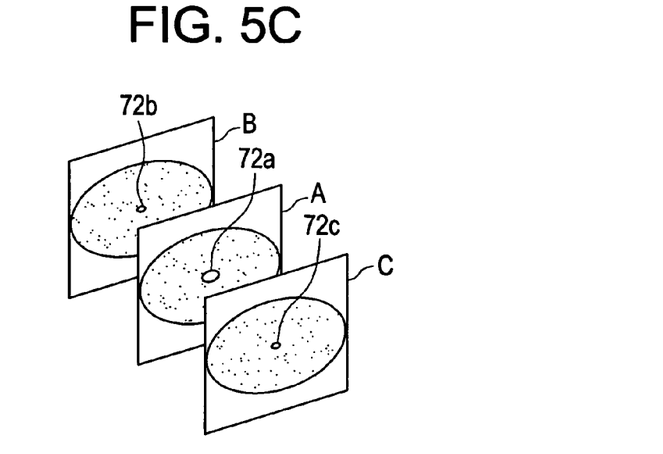

FIG. 5 is a diagram for explaining the inter-imaging-plane filtering processing step. In the drawing, FIG. 5(a) shows a condition before the inter-imaging-plane filtering processing step, in which three images A, B and C of a subject to be imaged 71 having therein a spherical object 72 are produced in an X-Y plane adjoining in a Z-axis direction, based on the image data. The first image A of the three images A, B and C has the spherical object 72 in the subject to be imaged 71 displayed in the center of the image, and the spherical object 72 is surrounded by noise. The second and third images B and C are produced based on the image data in imaging planes sandwiching the imaging plane for the first image A. Unlike the first image A, the second and third images B and C have an indefinite spherical object 72 in the subject to be imaged 71 in the center of the image, and have noise over the entire image. FIG. 5(b) shows a condition after the inter-imaging-plane smoothing processing step and inter-imaging-plane specific region extracting step in the inter-imaging-plane filtering processing step, representing that noise is reduced in the three images A, B and C. FIG. 5(c) shows a condition after the inter-imaging-plane smoothing processing step in the inter-imaging-plane filtering processing step.

Figure 6:
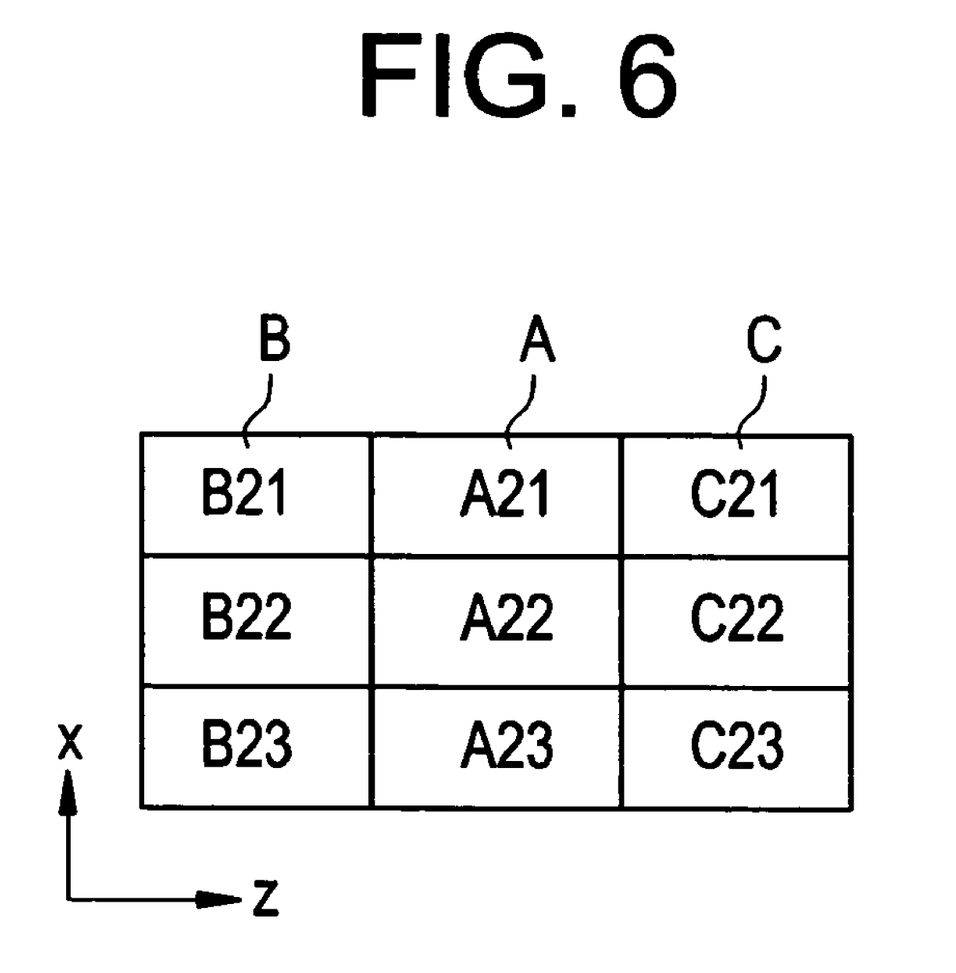
FIG. 6 is a diagram showing a pixel region to which the inter-imaging-plane filtering processing step is to be applied.

FIG. 6 is a diagram showing a pixel region to which the inter-imaging-plane filtering processing step is to be applied. In FIG. 6, there is shown adjoining image data in pixel regions corresponding to one another in the Z-axis direction, each pixel region extending in the X-axis direction of the X-Y plane, in the three images A, B and C in FIG. 5 adjoining in the Z-axis direction that corresponds to the body axis direction. The image data A21, A22 and A23 are image data in a predefined pixel region in the first image A, the image data B21, B22 and B23 are image data in the second image B corresponding to the image data A21, A22 and A23 in the predefined pixel region in the first image A, and the image data C21, C22 and C23 are image data in the third image C corresponding to the image data A21, A22 and A23 in the predefined pixel region in the first image A. Of these image data, the image data A22 in the first image A is based on the spherical object 72 in the subject to be imaged 71, and has a CT value as image data, for example, significantly different from those of the surrounding image data. The other image data A21, A23, B21, B22, B23, C21, C22 and C23, excluding the image data A22 in the first image A, are data representing a region in which the spherical object 72 in the subject to be imaged 71 is not present, and they contain numeric value data representing noise.

As shown in FIG. 4, at the intra-imaging plane filtering processing step, the image data A21, A22, A23, B21, B22, B23, C21, C22 and C23 corresponding to a plurality of cross-sectional planes of the subject to be imaged are first read and acquired from the storage device 34 into the central processing apparatus 31 (S41).

Then, the central processing apparatus 31 is used to calculate a difference for the image data between pixels in adjacent cross-sectional planes across a plurality of cross-sectional planes (S42). For example, as shown in FIG. 6, for the image data A22 in first image A based on the spherical object 72, differences ZA22$^-$ and ZA22$^+$ from the corresponding image data B22 and C22 in the cross-sectional planes in the Z-axis direction are calculated as follows: ZA22$^-$=A22−B22 and ZA22$^+$=A22−C22. In this manner, the differences between the corresponding image data in a predefined region in the Z-axis direction are calculated pixel by pixel. Alternatively, for the image data A22 in the first image A based on the spherical object 72, differences from eight elements of surrounding image data A21, A23, B21, B22, B23, C21, C22 and C23 may be calculated.

Next, the inter-imaging-plane specific region extracting means 53 is used to compare a difference calculated by the central processing apparatus 31 with a predetermined threshold for the difference to extract a specific pixel region across the plurality of cross-sectional planes (S43).

Among the nine elements of the image data A21, A22, A23, B21, B22, B23, C21, C22 and C23, the image data A22 of the first image A is based on the spherical object 72 in the subject to be imaged 71, and has a CT value as image data, for example, significantly different from those of other surrounding image data A21, A23, B21, B22, B23, C21, C22 and C23. Therefore, the sum of the differences ZA22$^-$ and ZA22$^+$ for the image data A22 of the first image A is larger than the sums of the respective differences calculated for the eight elements of image data A21, A23, B21, B22 B23, C21, C22 and C23 in a region that is not based on the spherical object 72 in the subject to be imaged 71. Thus, the region corresponding to the image data A22 representing the spherical object 72 in the subject to be imaged 71 can be extracted as a specific pixel region in the imaging plane based on a threshold predefined across the images A, B and C in a plurality of imaging planes.

Then, weighting factors for image data in the specific pixel region and for those in a pixel region other than the specific pixel region are calculated (S44). For example, the image data A22 extracted as the specific pixel region is given a factor K1 of large value, and the image data A21, A23, B21, B22, B23, C21, C22 and C23 outside the specific pixel region are given a factor K2 of smaller value than that for the image data A22. The image data in the specific pixel region and image data in a pixel region other than the specific pixel region are thus given different weighting factors.

Next, the inter-imaging-plane smoothing processing means 52 is used to calculate an average value for smoothing processing (S45). The smoothing processing calculates an average value between a prespecified pixel in an imaging plane and a pixel proximate to the prespecified pixel, and defines the average value as data for the prespecified pixel. For example, as shown in FIG. 6, for the image data A22 in the first image A in the specific pixel region, an average value VZA22 of the image data A22 with the corresponding image data B22 and C22 in a predefined range in the Z-axis direction containing the image data A22 itself is calculated as follows: VZA22=(A22+B22+C22)/3. On the other hand, for the image data B22 outside the specific pixel region, an average value VZB22 of the image data B22 with the corresponding image data A22 in a predefined range in the Z-axis direction containing the image data B22 itself is calculated as follows: VZB22=(A22+B22)/2. In this manner, an average value between corresponding image data in a predefined region in the Z-axis direction is calculated pixel by pixel. Alternatively, an average value of the image data A22 in the first image A based on the spherical object 72 may be calculated with eight elements of the surrounding image data A21, A23, B21, B22, B23, C21, C22 and C23.

Next, the weighting factor for the specific pixel region and that for the pixel region other than the specific pixel region, and the average values calculated by the smoothing processing are used to calculate products, and the products are defined as image data in the pixel region (S46). For example, in the specific pixel region including the image data A22, image data A'22 after the inter-imaging-plane filtering processing step is calculated by: A'22=K1·VZA22. On the other hand, outside the specific pixel region, for example, image data B'22 after the inter-imaging-plane filtering processing step is calculated by: B'22=K2· VZB22. As described above, the specific pixel region is given the factor K1 of large value, and the region other than the specific pixel region is given the factor K2 of smaller value than that for the specific pixel region. In this manner, image data after the inter-imaging-plane filtering processing step are calculated for the pixel regions.

By the aforementioned processing, three images A, B and C are obtained with reduced noise, as shown in FIG. 5(b), after conducting the inter-imaging-plane specific region extracting step and inter-imaging-plane smoothing processing step in the inter-imaging-plane filtering processing step. Of the three images A, B and C, the first image A has a region 72a containing image data based on the spherical object 72 in the subject to be imaged 71, resulting in a high-resolution and sharp image. FIG. 5(c) shows a condition after conducting the inter-imaging-plane smoothing processing step without conducting the inter-imaging-plane specific region extracting step in the inter-imaging-plane filtering processing step. Noise can be also reduced after conducting the inter-imaging-plane smoothing processing step. However, some original image data may give rise to regions 72b and 72c having image data different from that in the actual image, as shown in the second and third images B and C in FIG. 5(c), leading to reduced resolution; and therefore, the inter-imaging-plane specific region extracting step is preferably conducted.

The intra-imaging-plane filtering processing step is a step of conducting filtering processing on image data in the same imaging plane for the subject to be imaged. As such an intra-imaging-plane filtering processing step, an intra-imaging-plane smoothing processing step and an intra-imaging-plane specific region extracting step are executed. The intra-imaging-plane smoothing processing step is a step of conducting smoothing processing on image data in the same imaging plane for the subject to be imaged. The intra-imaging-plane specific region extracting step is a step of extracting a specific pixel region in the same imaging plane based on the image data representing the imaging plane and a predetermined threshold defined in the imaging plane for the subject to be imaged.

The intra-imaging-plane filtering processing step will now be described with reference to FIGS. 7 and 8.

Figure 7:
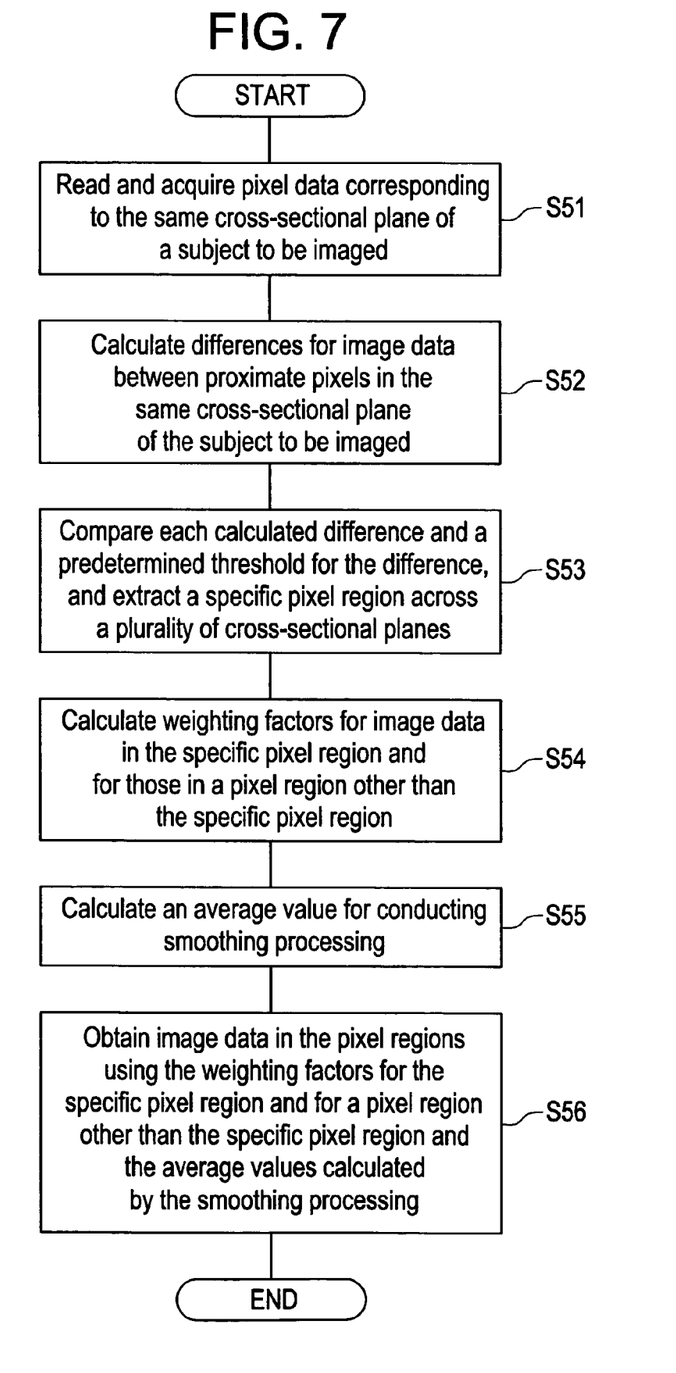
FIG. 7 is a process chart showing the procedure at an intra-imaging-plane filtering processing step.

FIG. 7 is a process chart showing the procedure at the intra-imaging-plane filtering processing step.

Figure 8:
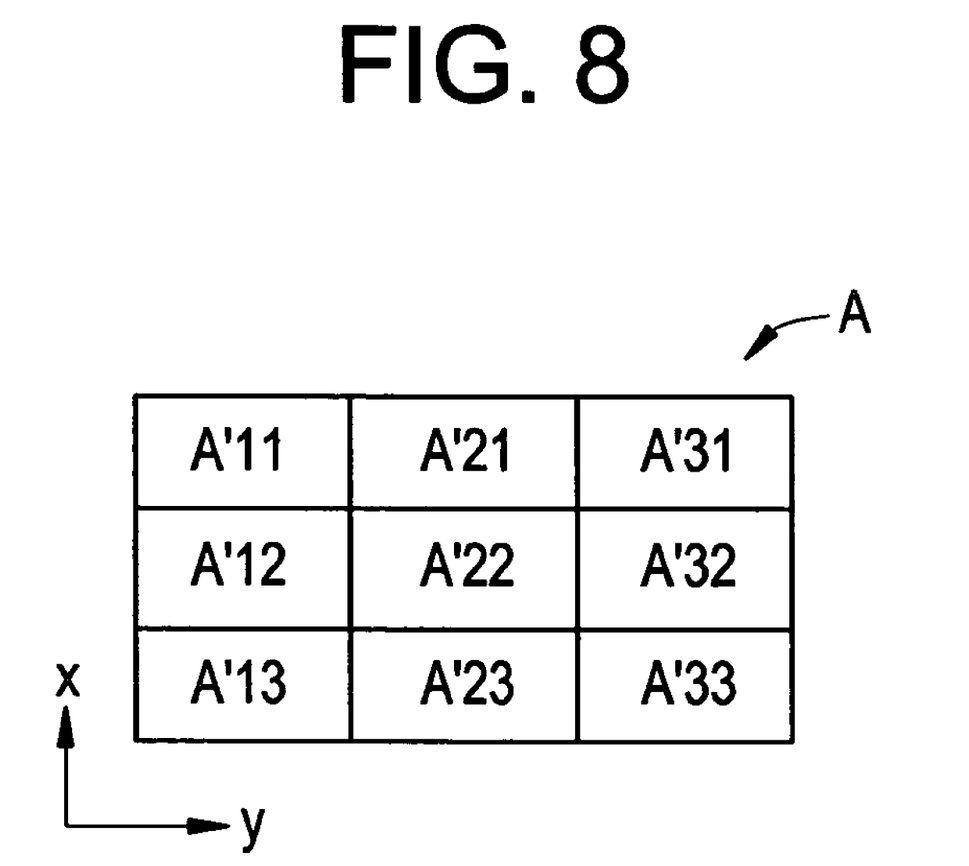
FIG. 8 is a diagram showing a pixel region to which the intra-imaging-plane filtering processing step is to be applied.

FIG. 8 is a diagram showing a pixel region to which the intra-imaging-plane filtering processing step is to be applied after the inter-imaging-plane filtering processing step. FIG. 8 shows, in an X-Y plane, nine elements of image data A'11, A'12, A'13, A'21, A'22, A'23, A'31, A'32 and A'33 of the first image A of the three images A, B and C adjoining in the Z-axis direction in FIG. 5 after the aforementioned intra-imaging-plane filtering processing step. Among these image data, image data A'22 is based on the spherical object 72 in the subject to be imaged 71, and has a CT value as image data, for example, significantly different from those of the surrounding image data. The other image data A'11, A'12, A'13, A'21, A'23, A'31, A'32 and A'33, excluding the image data A'22, in the first image A' are data representing a region in which the spherical object 72 in the subject to be imaged 71 is not present, and they contain numeric value data representing noise.

As shown in FIG. 7, at the intra-imaging-plane filtering processing step, image data A'11, A'12, A'13, A'21, A'22, A'23, A'31, A'32 and A'33 corresponding to the same cross-sectional plane of the subject to be imaged are first read and acquired from the storage device 34 into the central processing apparatus 31 (S51).

Then, the central processing apparatus 31 is used to calculate differences for the image data A'11, A'12, A'13, A'21, A'22, A'23, A'31, A'32 and A'33 between adjacent pixels in the same cross-sectional plane (S52). For example, as shown in FIG. 8, for the image data A'22 in the first image A based on the spherical object 72, differences $YA22^-$ and $YA22^+$ from the adjacent image data A'12 and A'32 in the y-axis direction are calculated as follows: $YA22^-$=A'22−A'12 and $YA22^+$=A'22−A'32. Similarly, for the image data A'22 in the first image A, differences $XA22^-$ and $XA22^+$ from the adjacent image data A'21 and A'23 in the x-axis direction are calculated as follows: $XA22^-$=A'22−A'21 and $XA22^+$=A'22−A'23. In this manner, differences between adjacent image data are calculated for the pixels in the y- and x-axis directions.

Next, the intra-imaging-plane specific region extracting means 63 is used to compare a difference calculated by the central processing apparatus 31 with a predetermined threshold for the difference to extract a specific pixel region in the same cross-sectional plane (S53).

Of the nine elements of the image data A'11, A'12, A'113, A'21, A'22, A'23, A'31, A'32 and A'33, the image data A'22 in the first image A is based on the spherical object 72 in the subject to be imaged 71, and has a CT value as image data, for example, significantly different from those of other surrounding image data A'11, A'12, A'13, A'21, A'23, A'31, A'32 and A'33. Therefore, the sum of the differences $YA22^-$, $YA22^+$, $XA22^-$ and $XA22^+$ for the image data A'22 in the first image A in the specific pixel region is larger than the sums of respective differences calculated for the eight elements of image data A'11, A'12, A'13, A'21, A'23, A'31, A'32 and A'33 in a region outside the specific pixel region. Thus, the region corresponding to the image data A'22 representing the spherical object 72 in the subject to be imaged 71 can be extracted as a specific pixel region in the imaging plane based on a threshold predefined in the same imaging plane.

Then, weighting factors for image data in the specific pixel region and for those in a pixel region other than the specific pixel region are calculated (S54). For example, the image data A'22 extracted as the specific pixel region is given a factor L1 of large value, and the image data A'11, A'12, A'13, A'21, A'23, A'31, A'32 and A'33 outside the specific pixel region are given a factor L2 of smaller value than that for the image data A'22. The image data in the specific pixel region and image data in a pixel region other than the specific pixel region are thus given different weighting factors.

Next, the intra-imaging-plane smoothing processing means 62 is used to calculate an average value for smoothing processing (S55). For example, as shown in FIG. 8, for the image data A'22 in the first image A in the specific pixel region, an average value VA'22 of the image data A'22 with the nine elements of the image data A'11, A'12, A'13, A'21, A'22, A'23, A'31, A'32 and A'33 in a predefined proximate range in the same X-Y plane containing the image data A'22 itself is calculated as follows: VA'22=(A'11+A'12+A'13+A'21+A'22+A'23+A'31+A'32+A'33)/9. On the other hand, for the image data A'12 outside the specific pixel region, an average value VA'12 of the image data A'12 with six elements of the image data A'11, A'12, A'13, A'21, A'22 and A'23 in a predefined proximate range in the same X-Y plane containing the image data A'12 itself is calculated as follows: VA'12=(A'11+A'12+A'13+A'21+A'22+A'23)/6. Thus, an average value among image data in a predefined proximate range in the same X-Y plane is calculated pixel by pixel.

Next, the weighting factor for the specific pixel region and that for the pixel region other than the specific pixel region, and the average values calculated by the smoothing processing are used to define image data in the pixel region (S56). The intra-imaging-plane filtering processing step can provide image data with further reduced noise. For example, in the specific pixel region including the image data A22, image data A"22 after the intra-imaging-plane filtering processing step is calculated by: A"22=L1·VA'22. On the other hand, outside the specific pixel region, for example, image data A"12 after the inter-imaging-plane filtering processing step is calculated by: A"12=L2·VA'12. As described above, the specific pixel region is given the factor L1 of large value, and the region other than the specific pixel region is given the factor L2 of smaller value than that for the specific pixel region. In this manner, image data after the intra-imaging-plane filtering processing step are calculated for the pixel regions.

As described above, the present embodiment acquires image data for a plurality of planes corresponding to a plurality of imaging planes for a subject to be imaged, and conducts filtering processing on the image data across the plurality of imaging planes. Since the amount of information on one pixel is increased by conducting filtering processing across a plurality of imaging planes, noise in an imaging plane can be reduced. Moreover, since a specific pixel region in an imaging plane is extracted based on a threshold predefined for image data across a plurality of imaging planes, resolution can be improved in the body axis direction. For example, when a lesion in a subject to be imaged is larger than 2-3 mm in size, and image data for four or more consecutive images with a slice thickness of about 0.5 mm are obtained in the body axis direction, the border of the lesion can be clearly displayed by complementing image data in the body axis direction in accordance with the present embodiment. The present invention is therefore effective especially when an imaging object is continuous in the body axis direction.

Furthermore, image data is also subjected to filtering processing in the same imaging plane for the subject to be imaged. The present embodiment can thus offer a combination of reduced image noise and improved resolution. Since the combination of reduced image noise and improved resolution is achieved by filtering processing without increasing the X-ray dose, exposure to the subject to be imaged can easily be reduced, and the apparatus life can easily be increased.

It should be noted that the present invention is not limited to being practiced in accordance with the aforementioned embodiment, and various modifications can be adopted.

For example, while a cross-sectional plane of the subject to be imaged is defined as an imaging plane and the filtering processing is conducted across imaging planes in the body axis direction in the aforementioned embodiment, the present invention may be applied to imaging planes moving in the time-axis direction, for example.

Moreover, while the smoothing processing is conducted by defining an average value in a predefined pixel region as image data in the aforementioned embodiment, a median value that is a center value in a predefined pixel region may be defined as image data.

Many widely different embodiments of the invention may be constructed without departing from the spirit and the scope of the present invention. It should be understood that the present invention is not limited to the specific embodiments described in the specification, except as defined in the appended claims.

The invention claimed is:

1. A radiation tomographic imaging apparatus comprising:
   a radiation emitting device for scanning a subject to be imaged around a body axis direction of said subject to be imaged and emitting radiation to an imaging region in said subject to be imaged;
   a radiation detecting device for detecting said radiation passing through said subject to be imaged; and
   an image producing device for generating image data representing said imaging region based on said detected radiation,
   wherein said image producing device comprises an inter-imaging-plane filtering processing device for acquiring said image data for a plurality of planes generated corresponding to imaging planes that are a plurality of cross-sectional planes of said imaging region, and conducting filtering processing on said image data across said plurality of imaging planes including a specified imaging plane within a range of a body axis direction to obtain smoothing processed image data of said specified imaging plane, wherein said smoothing processed image data are obtained for said plurality of said imaging planes.

2. The radiation tomographic imaging apparatus according to claim 1, wherein:
   said inter-imaging-plane filtering processing device comprises an inter-imaging-plane specific region extracting device for extracting a specific pixel region in said imaging plane based on image data representing said plurality of imaging planes and a threshold defined across said plurality of imaging planes.

3. The radiation tomographic imaging apparatus according to claim 2, wherein said inter-imaging-plane filtering processing device further comprises a device for multiplying a weighting factor coefficient to the smoothing processed pixel data of the specific pixel region and the pixel region other than the specific region, wherein said weighting factor is determined for respective regions.

4. The radiation tomographic imaging apparatus according to claim 1, wherein:
   said image producing device comprises an intra-imaging-plane filtering processing device for conducting filtering processing on said image data in the same imaging plane for said subject to be imaged.

5. The radiation tomographic imaging apparatus according to claim 4, wherein:
   said intra-imaging-plane filtering processing device comprises an intra-imaging-plane smoothing processing device for conducting smoothing processing on said image data in the same imaging plane for said subject to be imaged.

6. The radiation tomographic imaging apparatus according to claim 4, wherein:
   said intra-imaging-plane filtering processing device comprises an intra-imaging-plane specific region extracting device for extracting a specific pixel region in an imaging plane based on image data representing said imaging plane and a threshold defined in the same imaging plane for said subject to be imaged.

7. The radiation tomographic imaging apparatus according to claim 1, wherein:
   said radiation emitting device helically scans said subject to be imaged around and along the body axis direction of the subject to be imaged.

8. The radiation tomographic imaging apparatus according to claim 1, wherein:
   said radiation emitting device emits X-rays as said radiation.

9. The radiation tomographic imaging apparatus according to claim 1, wherein:
   said radiation detecting device has a plurality of radiation detector elements for detecting radiation passing through said subject to be imaged arranged in the body axis direction of said subject to be imaged.

10. A radiation tomographic imaging method that employs a radiation tomographic imaging apparatus comprising a radiation emitting device for scanning a subject to be imaged around a body axis direction of said subject to be imaged and emitting radiation to an imaging region in said subject to be imaged, and a radiation detecting device for detecting said radiation passing through said subject to be imaged, said method comprising:
    an image producing step of generating image data representing said imaging region based on radiation detected by said radiation detecting device; and
    a displaying step of displaying an image based on the image data,
    wherein said image producing step comprises an inter-imaging-plane filtering processing step of acquiring said image data for a plurality of planes generated corresponding to imaging planes that are a plurality of cross-sectional planes of said subject to be imaged, and conducting filtering processing on said image data across said plurality of imaging planes including a specified imaging plane within a range of a body axis direction to obtain smoothing processed image data of said specified imaging plane, wherein said smoothing processed image data are obtained for said plurality of said imaging planes.

11. The radiation tomographic imaging method according to claim 10, wherein:
    said inter-imaging-plane filtering processing step comprises an inter-imaging-plane specific region extracting step of extracting a specific pixel region in said imaging plane based on image data representing said plurality of imaging planes and a threshold defined across said plurality of imaging planes.

12. The radiation tomographic imaging method according to claim 11, wherein said inter-imaging-plane filtering processing method further comprises a step for multiplying a weighting factor coefficient to the smoothing processed pixel data of the specific pixel region and the pixel region other than the specific region, wherein said weighting factor is determined for respective regions.

13. The radiation tomographic imaging method according to claim 10, wherein;
    said image producing step comprises an intra-imaging-plane filtering processing step of conducting filtering processing on said image data in the same imaging plane for said subject to be imaged.

14. The radiation tomographic imaging method according to claim 13, wherein:

said intra-imaging-plane filtering processing step comprises an intra-imaging-plane smoothing processing step of conducting smoothing processing on said image data in the same imaging plane for said subject to be imaged.

15. An image producing apparatus for generating image data representing an imaging region in a subject to be imaged, comprising:

an image reconstructing device for generating said image data for a plurality of planes generated corresponding to a plurality of imaging planes of said imaging region; and an inter-imaging-plane filtering processing device for acquiring said image data for a plurality of planes generated corresponding to a plurality of imaging planes of said imaging region, and conducting filtering processing on said image data across said plurality of imaging planes including a specified imaging plane within a range of a body axis direction to obtain smoothing processed image data of said specified imaging plane, wherein said smoothing processed image data are obtained for said plurality of said imaging planes.

16. The image producing apparatus of according to claim 15, wherein said inter-imaging-plane filtering processing device comprises:

an inter-imaging-plane specific region extracting device for extracting a specific pixel region in said imaging plane based on image data representing said plurality of imaging planes and a threshold defined across said plurality of imaging planes.

17. The image producing apparatus according to claim 15, further comprising:

an intra-imaging-plane filtering processing device for conducting filtering processing on said image data in the same imaging plane for said subject to be imaged.

18. The image producing apparatus according to claim 17, wherein said intra-imaging-plane filtering processing device comprises:

an intra-imaging-plane smoothing processing device for conducting smoothing processing on said image data in the same imaging plane for said subject to be imaged.

19. The image producing apparatus according to claim 17, wherein said intra-imaging-plane filtering processing device comprises:

an intra-imaging-plane specific region extracting device for extracting a specific pixel region in an imaging plane based on image data representing said imaging plane and a threshold defined in the same imaging plane for said subject to be imaged.

* * * * *